US00PP11443P

United States Patent [19]

Kientzler

[11] Patent Number: Plant 11,443

[45] Date of Patent: Jul. 11, 2000

[54] NEW GUINEA IMPATIENS PLANT NAMED 'KIRAU'

[75] Inventor: Ludwig Kientzler, Gensingen, Germany

[73] Assignee: Paul Ecke Ranch, Inc., Encinitas, Calif.

[21] Appl. No.: 09/127,636

[22] Filed: Jul. 31, 1998

[51] Int. Cl.[7] ..... A01H 5/00

[52] U.S. Cl. ..... Plt./318

[58] Field of Search ..... Plt./318

[56] References Cited

U.S. PATENT DOCUMENTS

P.P. 6,731 4/1989 Keintzler ..... Plt./318
P.P. 8,406 10/1993 Trees ..... Plt./318

*Primary Examiner*—Howard J. Locker
*Assistant Examiner*—Wendy A Baker
*Attorney, Agent, or Firm*—C. A. Whealy

[57] ABSTRACT

A new and distinct cultivar of New Guinea Impatiens plant named 'Kirau', characterized by its numerous red-colored flowers; rounded and outwardly spreading growth habit; very freely branching, dense and bushy plant habit; and dark green leaves.

1 Drawing Sheet

BACKGROUND OF THE INVENTION

The present invention relates to a new and distinct cultivar of New Guinea Impatiens plant, botanically known as *Impatiens hawkeri*, and hereinafter referred to by the cultivar name Kirau.

The new cultivar is a product of a planned breeding program conducted by the Inventor in Gensingen, Germany. The objective of the breeding program was to develop early-flowering varieties with numerous flowers, uniform plant habit, attractive flower and foliage colors, and good flower form.

The new cultivar originated from a cross made by the Inventor of the proprietary selection identified as MF 242 as the male, or pollen parent, with the proprietary selection identified as MF 73 as the female, or seed parent.

The cultivar Kirau was discovered and selected by the Inventor as a flowering plant within the progeny of the stated cross in a controlled environment in Gensingen, Germany, in April, 1996.

Asexual reproduction of the new cultivar by terminal cuttings taken at Gensingen, Germany, has shown that the unique features of this new Impatiens are stable and reproduced true to type in successive generations of asexual reproduction.

SUMMARY OF THE INVENTION

The following traits have been repeatedly observed and are determined to be the unique characteristics of 'Kirau'. These characteristics in combination distinguish 'Kirau' as a new and distinct cultivar:

1. Numerous red-colored flowers.
2. Rounded and outwardly spreading growth habit.
3. Very freely branching, dense and bushy plant habit.
4. Dark green leaves.

Plants of the new New Guinea Impatiens are smaller and have smaller flowers and brighter green leaves than plants of the male parent, the proprietary selection identified as MF 242.

Compared to plants of the female parent, the proprietary selection identified as MF 73, plants of the new New Guinea Impatiens are larger and have larger and more rounded flowers.

Plants of the new New Guinea Impatiens are similar in flower color to plants of the cultivar Tarawa, disclosed in U.S. Plant Pat. No. 10,320. However, in side-by-side comparisons conducted in Encinitas, Calif., plants of the new New Guinea Impatiens differed from plants of the cultivar Tarawa in the following characteristics:

1. Plants of the new New Guinea Impatiens are more rounded and slightly more compact than plants of the cultivar Tarawa.

2. Plants of the new New Guinea Impatiens have smaller leaves than plants of the cultivar Tarawa.

3. Lower surfaces of leaves of plants of the new New Guinea Impatiens are green in color whereas lower surfaces of leaves of plants of the cultivar Tarawa are red purple in color.

4. Flowers of plants of the new New Guinea Impatiens are not as flat as flowers of plants of the cultivar Tarawa.

5. Peduncles of plants of the new New Guinea Impatiens are longer and hold the flowers higher above the foliage than peduncles of plants of the cultivar Tarawa.

A detailed comparison of plants of the cultivars Kirau and Tarawa appears in Chart A at the end of the specification.

BRIEF DESCRIPTION OF THE PHOTOGRAPHS

The accompanying colored photographs illustrate the overall appearance of the new cultivar, showing the colors as true as it is reasonably possible to obtain in colored reproductions of this type. Colors in the photographs may differ slightly from the color values cited in the detailed botanical description which more accurately describe the actual colors of the new New Guinea Impatiens.

The photograph at the top of the sheet comprises a top perspective view of a typical plant of 'Kirau'.

The photograph at the bottom of the sheet comprises a comparison close-up view of typical flowers and leaves of the cultivars Kirau (left) and Tarawa (right). Flower and foliage colors in the photographs may differ from the actual colors due to light reflectance.

DETAILED BOTANICAL DESCRIPTION

Plants of the cultivar Kirau have not been observed under all possible environmental conditions. The phenotype may vary somewhat with variations in environment such as temperature and light intensity, without, however, any variance in genotype. The following observations, measurements and comparisons describe three plants measured separately in 25-cm hanging baskets in Encinitas, Calif., under commercial practice in a polyethylene-covered greenhouse with day temperatures ranging from 21 to 32° C. and night temperatures ranging from 16 to 18° C. and light levels of about 3,500 footcandles.

In the following description, color references are made to The Royal Horticultural Society Colour Chart except where general terms of ordinary dictionary significance are used.

Classification:

*Botanical.*—*Impatiens hawkeri* cultivar Kirau.

*Commercial.*—New Guinea Impatiens cultivar Kirau.

Parentage:

*Male parent.*—Proprietary selection of *Impatiens hawkeri* identified as MF 242.

*Female parent.*—Proprietary selection of *Impatiens hawkeri* identified as MF 73.

Propagation:

*Type cutting.*—Terminal cuttings.

*Time to initiate roots.*—Summer: About 14 days with 21° C. soil temperature. Winter: About 18 days with 21° C. soil temperature.

*Time to develop roots.*—Summer: About 21 days with 21° C. soil temperature. Winter: About 24 days with 21° C. soil temperature.

Plant description:

*Plant form.*—Outwardly spreading, rounded.

*Growth habit.*—Vigorous. Very freely branching, dense and bushy growth. Appropriate for 10 to 25-cm containers.

*Crop time.*—From planting of a rooted cutting, about eight weeks are required to produce a finished flowering plant in a 12.5-cm container.

*Plant size.*—Height: About 24 cm. Width or spread: About 32 cm.

*Lateral branches.*—Quantity: About 9. Length: About 15 cm. Diameter: About 7 mm. Internode length: About 4.25 cm. Color: 59A.

*Foliage description.*—Leaves simple, generally symmetrical, abundant, opposite or in whorls, horizontal to plant. Mostly flat. Length: About 8.75 cm. Width: About 3.25 cm. Shape: Elliptic with acuminate apex, attenuate base and serrulate margin with ciliation. Texture: Smooth, glossy. Color: Young foliage, upper surface: 144A. Young foliage, lower surface: 138B. Fully expanded foliage, upper surface: 147A. Fully expanded foliage, lower surface: 147C. Venation, upper surface: 59B. Venation, lower surface: 59A. Petiole: Length: About 3.75 cm. Diameter: About 3 mm. Color: 59B.

Flower description:

*Flower type and habit.*—Red-colored flowers. Freely and continuously flowering. Flowers arise from leaf axils. Usually about 12 flowers and flower buds per lateral branch. Flowers positioned mostly above the foliage and face upward and outward. Flowers slightly cupped and rounded triangle. Flowers persistent.

*Flowering season.*—Year-round under greenhouse conditions. In the garden, flowering is continuous from spring until fall. Flowers typically last less than one week depending on environmental and cultural conditions.

*Flower size.*—Length, vertical axis: About 5.5 cm. Width, horizontal axis: About 5.8 cm. Depth: About 1.5 cm.

*Flower buds.*—Length: About 1.6 cm. Diameter: About 9 mm. Shape: Ovoid. Color: 44B.

*Petals.*—Quantity: Five. Length: Upper petal: About 3 cm. Middle petals: About 2.9 cm. Lower petals: About 3.3 cm. Width: Upper petal: About 5 cm. Middle petals: About 3.2 cm. Lower petals: About 3.7 cm. Shape: Cordate with acute base and entire margin. Texture: Velvety, smooth. Color: When opening, upper surface: Brighter than 44A. When opening, lower surface: 44B. Fully opened, upper surface: 44A; color does not fade. Fully opened, lower surface: 40A.

*Spur.*—Length: About 4.75 cm. Shape: Narrow and curved. Color: 60A/60B.

*Peduncles.*—Length: About 6.3 cm. Angle: Acute, outward. Strength: Strong. Color: 59A.

*Reproductive organs.*—Androecium: Stamen number: Five, anthers fused, filaments free. Anther shape: Obovate. Anther size: 4 mm by 5 mm. Anther color: 2D. Amount of pollen: Moderate. Pollen color: 4D. Gynoecium: Five-loculate fused. Pistil length: About 5 mm. Stigma color: 4D. Ovary color: 144A.

Disease resistance: Under commercial conditions, resistance to pathogens has not been observed.

Seed development: Seed production has not been observed.

CHART A

| CHARACTERISTIC | 'KIRAU' | 'TARAWA' |
|---|---|---|
| PLANT HEIGHT | About 24 cm | About 25 cm |
| LATERAL BRANCH LENGTH | About 15 cm | About 16 cm |
| LEAF LENGTH | About 8.75 cm | About 9.5 cm |
| LEAF WIDTH | About 3.25 cm | About 3.7 cm |
| LEAF COLOR, IMMATURE, LOWER SURFACE | 138B | 59A |
| LEAF COLOR, MATURE, LOWER SURFACE | 147C | 59A/59B |
| PEDUNCLE LENGTH | About 6.3 cm | About 5.4 cm |
| PEDUNCLE COLOR | 59A | 60A |

It is claimed:

1. A new and distinct cultivar of New Guinea Impatiens plant named 'Kirau', as illustrated and described.

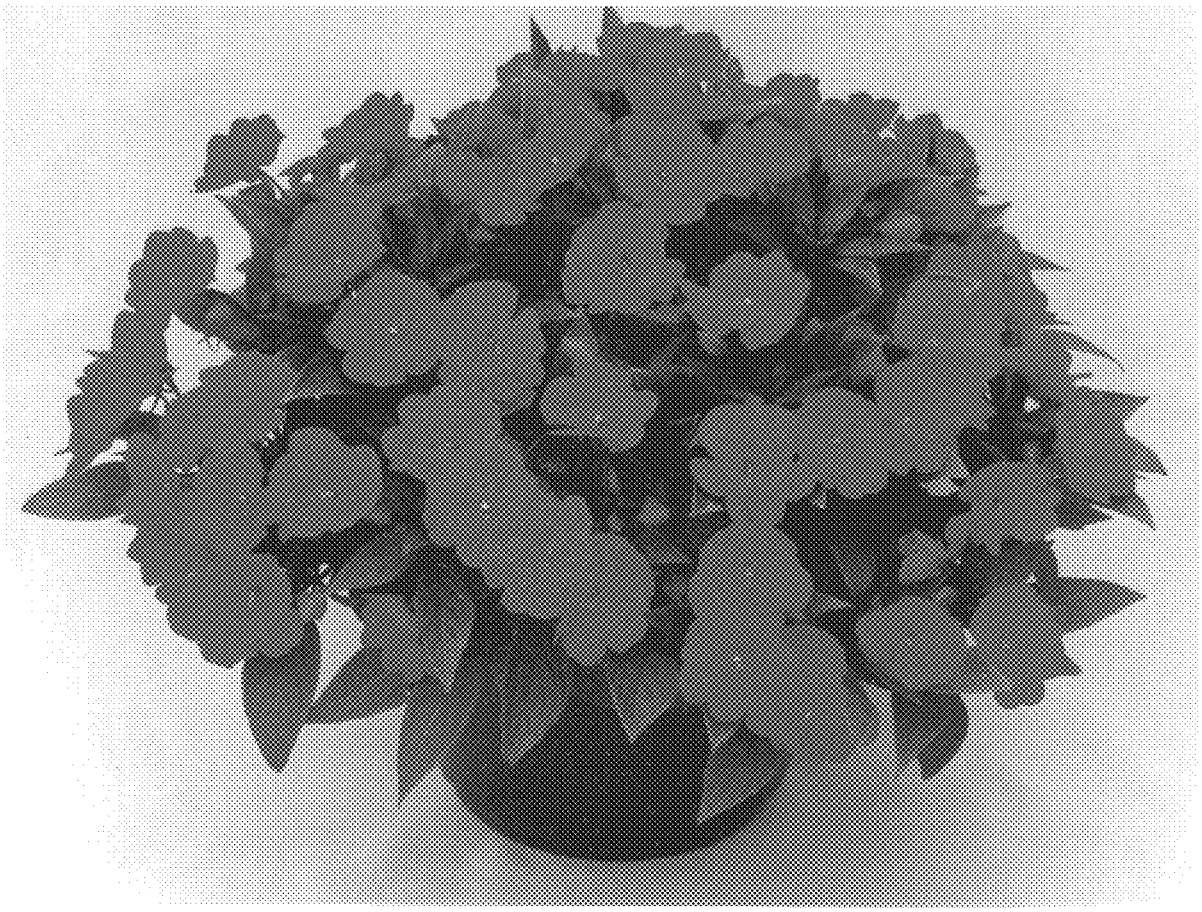
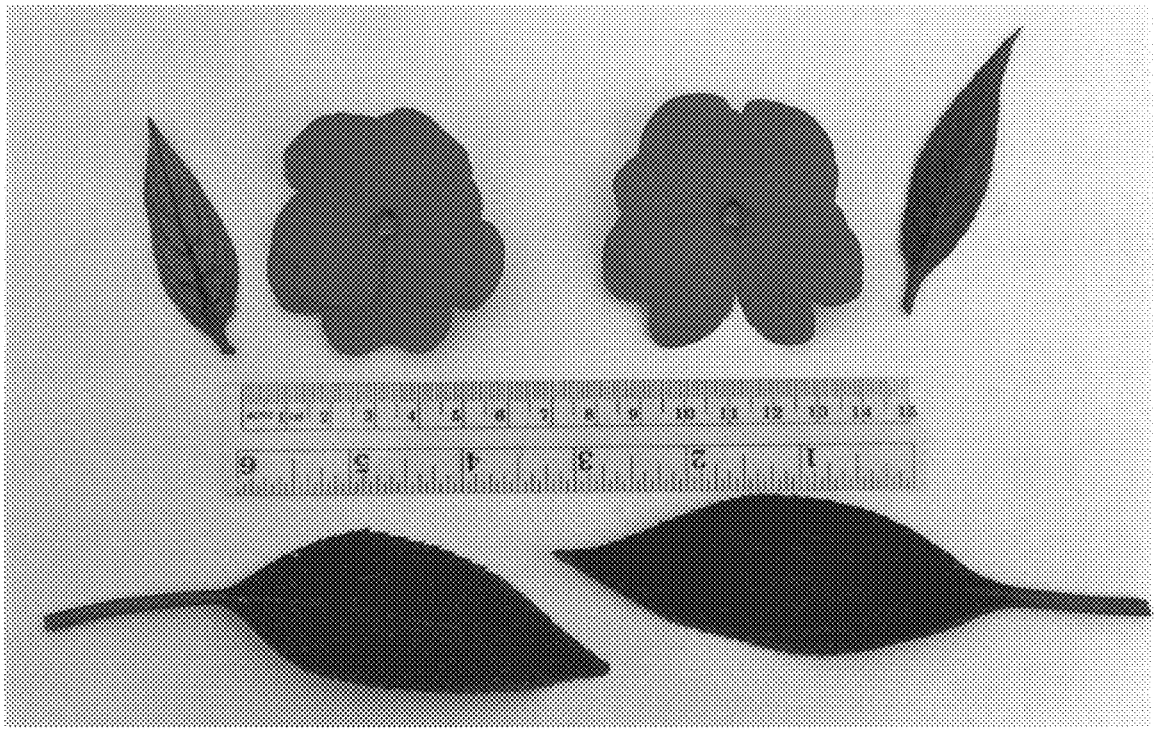

* * * * *